United States Patent [19]

Awamura et al.

[11] Patent Number: 4,943,431
[45] Date of Patent: Jul. 24, 1990

[54] EMULSIFIED HAIR COSMETIC

[75] Inventors: Masaki Awamura, Takatsuki; Kazushi Yamamoto, Osaka; Masashi Nanjo, Kawanishi, all of Japan

[73] Assignee: Sunstar Kabushiki Kaisha, Osaka, Japan

[21] Appl. No.: 286,638

[22] Filed: Dec. 19, 1988

[30] Foreign Application Priority Data

Dec. 24, 1987 [JP] Japan .................... 62-329340

[51] Int. Cl.$^5$ .................... A61K 7/08; A61K 7/06
[52] U.S. Cl. .................... 424/70; 514/772; 424/78
[58] Field of Search .................... 424/70, 78, 71; 514/772

[56] References Cited

FOREIGN PATENT DOCUMENTS 0226337 6/1987 European Pat. Off. .
0285364 10/1988 European Pat. Off. .
222109 9/1988 Japan .

Primary Examiner—Thurman K. Page
Assistant Examiner—Susan S. Rucker
Attorney, Agent, or Firm—Wegner & Bretschneider

[57] ABSTRACT

An emulsified hair cosmetic providing excellent easy combing and a feeling of smoothness to hair and protecting hair against heat and brushing which comprises a dimethylsilicone rubber of the formula

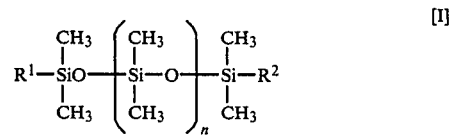

[I]

wherein $R^1$ and $R^2$ are methyl or hydroxyl; and n is an integer of 4000 to 9000, polyalcohol and nonionic surfactant.

2 Claims, No Drawings

EMULSIFIED HAIR COSMETIC

FIELD OF THE INVENTION

The present invention relates to an emulsified hair cosmetic providing excellent easy combing and a feeling of smoothness to hair and protecting hair against heat and brushing.

BACKGROUND OF THE INVENTION

Various hair treating compositions such as a hair treatment preparation, a hair rinse, etc. have been used to provide gloss and elasticity to hair, or to take care of injured hair. For example, in order to provide gloss to hair, a hair treating composition in which oily ingredients such as silicone oil, higher alcohol, liquid paraffin, ester oil, etc. are formulated have been used. Further, in order to provide softness and antistatic effect to hair, a hair treating composition in which a cationic surfactant or a cationic high polymer is formulated have been used. Furthermore, in order to protect hair against heat of drier, etc., a hair treating composition in which a water-soluble high polymer is formulated have been used.

However, when a hair treating composition in which the above oily ingredients are formulated is applied to hair, it provides a feeling of extraneous matter such as sticking. The hair treating composition itself also causes sticking, therefore the physical resistance against combing or brushing becomes large. Further, a hair treating composition in which a cationic surfactant, a cationic high polymer is formulated electrically adsorbs only at part of the surface of hair, charged negative, so that the adsorptivity is not enough and the homogeneity and the combing are not satisfactory. Furthermore, a hair treating composition itself in which a water-soluble high polymer is formulated cause a remarkable sticking and adhesion, therefore after treatment it provides a feeling of extraneous matter such as stiffness and the combing is not satisfactory.

In addition, a hair care product using a silicone rubber and, further, a skin care composition having water resistance and permanence properties in which a dimethyl silicone rubber is formulated (see Japanese Laid Open Publication No. 229810/1986) have been proposed. But they have the large physical resistance against combing and a feeling of sticking. Moreover, it is very difficult to emulsify a silicone rubber because it is insoluble in water and ethanol and very slightly soluble in an oily ingredient such as liquid paraffin etc.

OBJECTS OF THE INVENTION

The main object of the present invention is to provide an emulsified hair cosmetic providing excellent easy combing and a feeling of smoothness to hair and protecting hair against heat and brushing.

This object as well as other objects and advantages of the present invention will become apparent to those skilled in the art from the following description.

SUMMARY OF THE INVENTION

According to the present invention, there is provided an emulsified hair cosmetic which comprises (i) a dimethylsilicone rubber of the formula:

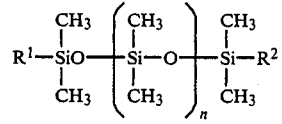

wherein $R^1$ and $R^2$ are methyl or hydroxy and n is an integer of 4000 to 9000

(ii) one or more polyalcohols selected from the group consisting of propylene glycol, 1,3-butylene glycol and glycerin: and (iii) one or more nonionic surfactants selected from the group consisting of polyoxyethylene oleyl ether, polyoxyethylene cetyl ether, ethylene glycol stearate, diethylene glycol stearate, polyethylene glycol stearate, polyethylene glycol distearate and glyceryl stearate, the total amount of (iii) not being more than 4 times the amount of (i) and not being less than 0.5 times the amount of (ii) and not more than 2 times the amount of (ii).

The emulsified hair cosmetic of the present invention provides excellent easy combing and smooth feeling to hair and protects hair against heat and brushing.

DETAILED DESCRIPTION OF THE INVENTION

The dimethyl silicone rubber used in the emulsified hair cosmetic of the present invention is represented by the following formula [I]:

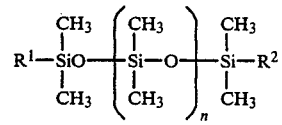

wherein $R^1$ and $R^2$ are methyl or hydroxy, and n is an integer of 4000 to 9000.

Representative examples of dimethyl silicone rubber of the formula [1] include Toshiba Silicone TSE-200 and TSE-200A manufactured by Toshiba Silicone Co., Ltd., Japan and the like, and one or more of them can be formulated in the emulsified hair cosmetic of the present invention in an amount of 0.01 to 10% by weight, preferably 0.5 to 2.0% by weight based on the total weight of the cosmetic. When the amount is less than 0.01% by weight, the effect for providing easy combing and a feeling of smoothness to hair becomes insufficient and, when the amount is more than 10% by weight, viscosity of the dimethyl silicone rubber itself increases and it becomes difficult to emulsify.

Further, one or more of the above surfactants (iii) as nonionic surfactant can be formulated in the emulsified hair cosmetic of the present invention. The total amount of such surfactant is not more than 4 times the amount of the silicone rubber of (i) and is not less than 0.5 times the amount of the polyalcohol of (ii) and not more than twice that.

When the total amount of (iii) is 4-fold more than the amount of silicone rubber, the emulsification is stabilized but usability of the emulsion is adversely effected. Further, when the total amount of nonionic surfactant of (iii) is out of the range of 0.5-fold to 2-fold amount of polyalcohol of (ii), the emulsion becomes unstable (the emulsion becomes liable to separate with dry).

Furthermore, oily ingredients (e.g., cyclic silicone, triglyceride, ester oil, wax, etc.), coloring agents, perfumery, pH adjustors (e.g., phosphoric acid, citric acid, etc.), humectants (e.g., pyrrolidone carboxylate, lactic acid, etc.), solvent (e.g., water, ethanol), antistatic agents (e.g., cationic surfactant) can be formulated in the emulsified hair cosmetic of the present invention so far as they do not deteriorate the properties of the composition.

The emulsified hair cosmetic of the present invention can be in the form of milky lotion, a blow-wave preparation, a hair treatment preparation or the like and can be produced by a know method. For example, the polyalcohol is mixed with the nonionic surfactant, if necessary, with heating. Then, a small amount of water (e.g., the same amount as the surfactant) is added to the resulting mixture. Separately, the dimethylsilicone rubber is dissolved in a suitable solvent (e.g., silicone oil having a low viscosity, ester oils, hydrocarbons, etc.). The resulting solution is slowly added with stirring to the above mixture. After completion of the addition, the remaining water is added thereto.

The hair cosmetic of the present invention can be used by the same manner as a conventional hair cosmetic.

The following Examples and Comparative Examples further illustrated the present invention in detail but are not to be construed to limit the scope thereof. All the %'s in Examples and Comparative Examples are by weight.

EXAMPLES 1 TO 6 AND COMPARATIVE EXAMPLES 1 TO 7

Each milky lotion like hair cosmetic was prepared by mixing the ingredients described in Table 1 and thereafter stirring according to a conventional method. The following items were evaluated by the use of these hair cosmetics. The results are also shown in Table 1.

Evaluation

Evaluation of a test sample was carried out according to the following method.

(1) Sticking immediately after application

Sticking immediately after application was evaluated by organoleptic test of practical use involving five professional panelists (female in the twenties).

(2) Resistance against combing after drying

A human hair (2 g) treated with each test treating composition and dried was attached to a rheometer (Fudo Kogyo Co., Ltd., Japan). Maximum drag applied to the rheometer upon combing was measured and resistance against combing was calculated from the following formula:

$$\text{Resistance against combing (\%)} = \frac{\text{Resistance against combing after treatment}}{\text{Resistance against combing before treatment}} \times 100$$

(3) The number of hair cut

The number of hair cut after 7200 times of combing (a bundle of hair weighed about 2 g: 119 non-treated hairs)

(4) Stability

After being allowed to stand at 40° C. for one month, separation (or creaming) was evaluated according to the following criteria.

O: Stable
x: Creaming or separation (5) Overall evaluation

O: no sticking, easy combing and stable
x: Sticking, bad combing or unstable

TABLE 1

| | Ingredients | Examples 1 | 2 | 3 | 4 | 5 | 6 | Comparative Examples 1 | 2 | 3 | 4 | 5 | 6 | 7 |
|---|---|---|---|---|---|---|---|---|---|---|---|---|---|---|
| i | Dimethyl silicone rubber ($R^1$ and $R^2$ = $CH_3$) | 1.0 | — | 0.8 | — | 1.0 | — | — | — | 1.0 | — | 0.8 | — | 0.8 |
| | Dimetyl silicone rubber ($R^1$ and $R^2$ = OH) | — | 1.0 | — | 0.8 | — | 1.5 | — | — | — | 1.0 | — | 0.8 | — |
| | Polyoxyethylene oleyl ether (5EO) | 1.2 | — | — | — | 0.5 | — | 1.2 | — | — | 1.2 | — | 1.2 | 1.2 |
| iii | Polyoxyethylene cetyl ether (10EO) | — | 0.3 | — | — | 0.2 | — | — | 0.2 | — | — | 3.0 | — | — |
| | Ethylene glycol stearate | — | — | 1.2 | — | — | — | — | — | — | — | — | — | — |
| | Diethylene glycol stearate | — | 0.8 | — | — | 0.3 | 1.0 | — | 0.3 | — | — | 1.0 | — | — |
| | Polyoxyethylene stearate (20EO) | — | — | — | 1.2 | — | — | — | — | — | — | — | — | — |
| | Propylene glycol | 1.0 | 1.0 | — | — | 0.5 | 0.5 | 1.0 | 0.5 | 1.0 | — | 1.0 | 5.0 | 0.5 |
| ii | 1,3-Butylene glycol | — | — | — | 1.0 | — | 1.0 | — | — | — | — | 0.5 | — | — |
| | Glycerin | — | — | 1.0 | — | 0.5 | — | — | 0.5 | — | — | — | — | — |
| | Decamethylcyclopentasiloxane | 5.0 | 5.0 | 5.0 | 5.0 | 5.0 | 5.0 | 5.0 | 5.0 | 5.0 | 5.0 | 5.0 | 5.0 | 5.0 |
| | Isopropyl palmitate | 1.0 | 1.0 | 1.0 | 1.0 | 1.0 | 1.0 | 1.0 | 1.0 | 1.0 | 1.0 | 1.0 | 1.0 | 1.0 |
| | Tween 80 | — | — | — | — | — | — | — | — | 1.2 | — | — | — | — |
| | Ethyl alcohol | 5.0 | 5.0 | 5.0 | 5.0 | 5.0 | 5.0 | 5.0 | 5.0 | 5.0 | 5.0 | 5.0 | 5.0 | 5.0 |
| | Water | | | | | | | remainder | | | | | | |
| | Sticking immediately after application | O | O | O | O | O | O | X | X | O | — | X | O | — |
| | Resistance against combing (%) | 60.3 | 58.8 | 61.3 | 63.2 | 55.6 | 57.2 | 103.1 | 99.5 | 61.4 | — | 83.3 | 70.5 | 68.2 |
| Result | Resistance against combing (after shampoo, %) | 71.2 | 70.0 | 67.4 | 73.2 | 72.1 | 68.8 | 100.5 | 105.1 | 67.3 | — | 70.8 | 77.3 | 72.5 |
| | The number of hair cut | 3 | 1 | 5 | 2 | 0 | 2 | 121 | 110 | 1 | — | 23 | 19 | 11 |
| | Stability | O | O | O | O | O | O | O | O | X | X | O | X | X |
| | Overall evaluation | O | O | O | O | O | O | X | X | X | X | X | X | X |

EXAMPLE 7

(a blow-wave preparation)

| Ingredient A | | Amount (%) |
|---|---|---|
| (1) | Propylene glycol | 0.8 |
| (2) | Polyoxyethylene oleyl ether (5 EO) | 0.5 |
| (3) | Polyoxyethylene stearate (2 EO) | 0.2 |
| (4) | Dimethyl silicone rubber (TSE 200A) | 0.8 |
| (5) | Polyoxyethylene lauryl ether sulfuric acid sodium salt | 0.1 |
| (6) | Hexamethylcyclotrisiloxane | 8.0 |
| Ingredient B | | Amount (%) |
| (7) | Water | remainder |
| Ingredient C | | Amount (%) |
| (8) | 95% Ethanol | 20 |
| Ingredient D | | Amount (%) |
| (9) | Perfume | 0.1 |

To the ingredients (1) to (3), (5) and a part of (7) (about 0.8%) were mixed. The ingredient (4) was dissolved in the ingredient (6) and the solution and the ingredient (9) were slowly added with stirring to the above mixture. Then, the remainder of (7) was added to prepare a blow-wave preparation.

EXAMPLE 8

(a milky lotion type)

| Ingredient A | | Amount (%) |
|---|---|---|
| (1) | 1,3-Butylene glycol | 1.8 |
| (2) | Polyoxyethylene cetyl ether (5 EO) | 1.2 |
| (3) | Methyl silicone rubber (TSE 200) | 1.0 |
| (4) | Decamethylcyclopentasiloxane | 19.0 |
| Ingredient B | | Amount (%) |
| (5) | Carbopol 941 | 0.3 |
| (6) | Water | remainder |
| Ingredient C | | Amount (%) |
| (7) | Triethanolamine | 0.3 |
| (8) | Water | 2.7 |
| Ingredient D | | Amount (%) |
| (9) | Perfume | 0.1 |

The ingredients (1), (2) and a part of (6) (1.0%) were mixed, if necessary, with heating. The ingredient (3) was dissolved in the ingredient (4) and the solution and the ingredient (9) were slowly added with stirring to the above mixture. The ingredients (5) and (6) were mixed. The ingredients (7) and (8) were mixed. Both mixture of the ingredients (5) and (6) as well as (7) and (8) were added to the above mixture to prepare a hair milky lotion.

EXAMPLE 9

(a hair rinse)

| | | Amount (%) |
|---|---|---|
| Ingredient A | | |
| (1) | Stearyltrimethylammonium chloride | 2.0 |
| (2) | Dimethyl silicone rubber (TSE200A) | 2.0 |
| (3) | Octamethylcyclotetrasiloxane | 8.0 |
| (4) | Self-emulsifiable glyceryl monostearate | 1.0 |
| (5) | Ethylene glycol monostearate | 1.0 |
| Ingredient B | | |
| (6) | Glycerin | 2.0 |
| (7) | Preservative | trace |
| (8) | Coloring agent | trace |
| (9) | Water | remainder |
| Ingredient C | | |
| (10) | Perfume | 0.1 |

The ingredients (1), (4) to (8) and a part of (9) (2.0%) were mixed with warming. The ingredient (2) was dissolved in (3) and the solution and the ingredient (10) were slowly added with stirring to the resulting mixture. The reminder of the ingredient (9) was added to the mixture to prepare a hair rinse.

What is claimed is:

1. An emulsified hair cosmetic which comprises
   (i) a dimethylsilicone rubber of the formula:

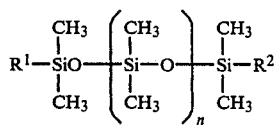

[I]

wherein $R^1$ and $R^2$ are methyl or hydroxyl and n is an integer of 4000 to 9000;
   (ii) one or more polyalcohols selected from the group consisting of propylene glycol, 1,3-butylene glycol and glycerin; and
   (iii) one or more nonionic surfactants selected from the group consisting of polyoxyethylene oleyl ether, polyoxyethylene cetyl ether, ethylene glycol stearate, diethylene glycol stearate, polyethylene glycol stearate, polyethylene glycol distearate and glyceryl stearate, the total amount of (iii) being not more than 4 times the amount of (i) and not being less than 0.5 times the amount of (ii) and not more than twice the amount of (ii).

2. An emulsified hair cosmetic according to claim 1, wherein the amount of the ingredient (i) is 0.01 to 10% by weight.

* * * * *